United States Patent [19]

Lormeau et al.

[11] Patent Number: 5,314,876
[45] Date of Patent: May 24, 1994

[54] HIGH MOLECULAR MASS N,O-SULPHATED HEPAROSANS, PROCESS FOR THEIR PREPARATION AND THE PHARMACEUTICAL COMPOSITIONS WHICH CONTAIN THEM

[75] Inventors: Jean-Claude Lormeau, Kremlin Bicetre; Bruno Chevallier, Villejuif; Marc L. V. Salome, Castanet-Tolosan, all of France

[73] Assignee: Elf Sanofi, Paris, France

[21] Appl. No.: 983,371

[22] Filed: Nov. 30, 1992

[30] Foreign Application Priority Data

Nov. 28, 1991 [FR] France ................... 91 14725

[51] Int. Cl.$^5$ ............. C08B 37/00; C12P 19/04; C12N 1/20; D61K 31/725
[52] U.S. Cl. ................................ 514/56; 536/21
[58] Field of Search ............... 536/21; 514/56

[56] References Cited

U.S. PATENT DOCUMENTS 4,818,817  4/1989  Shoham et al. .................. 536/1.1

FOREIGN PATENT DOCUMENTS 0333243  9/1989  European Pat. Off. .
0489647  6/1992  European Pat. Off. .
2584728  1/1987  France .
9217507  10/1992  World Int. Prop. O. .

OTHER PUBLICATIONS

Abs. Biotech 92-10267 EP. 489647 (Jun. 10, 1992) Elf-Sanofi.
Risenfeld et al., "Biosynthesis of Heparin. Effect of Detergent on the Microsomal Polymerization & Polymer Modification Processes", Glycoconjugate, vol. 4, pp. 179–189, 1987.
Kusche et al., "Biosynthesis of Heparin. Use of Escherichia coli K5 capsular polysaccharide as a Model Substrate in Enzymic Polymer-Modification . . . ", Biochem. J., vol. 275, pp. 151–158, Apr. 1991.

*Primary Examiner*—Herbert J. Lilling
*Attorney, Agent, or Firm*—Wegner, Cantor, Mueller & Player

[57] ABSTRACT

The subject of the invention is new high molecular mass N,O-sulphated heparosans consisting of chains or of a mixture of chains having a molecular mass of between $1.5 \times 10^4$ and $4.0 \times 10^6$ D, characterised by a repeating disaccharide structure of formula I:

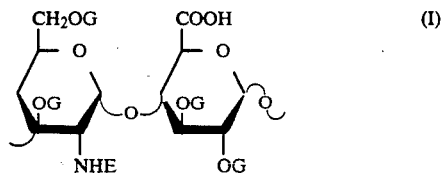

in which E represents, in 0 to 80% of the disaccharide units of the said N,O-sulphated heparosan, an acetyl group and, in the remaining disaccharide units, a sulphate group and optionally a hydrogen atom, G represents a hydrogen atom and a sulphate group, and the pharmaceutically acceptable salts of the said N,O-sulphated heparosans.

13 Claims, No Drawings

HIGH MOLECULAR MASS N,O-SULPHATED HEPAROSANS, PROCESS FOR THEIR PREPARATION AND THE PHARMACEUTICAL COMPOSITIONS WHICH CONTAIN THEM

The subject of the present invention is new high molecular mass N,O-sulphated heparosans, the N,O-sulphated heparosan compositions containing these new N,O-sulphated heparosans, and the pharmaceutical compositions which have the new high molecular mass N,O-sulphated heparosans as active principle.

It is known that glycosaminoglycans are products capable of being obtained by extraction from animal tissues. Certain of these glycosaminoglycans have very advantageous anticoagulating and antithrombotic properties. Typical products of this family are heparin, its cleavage products and their derivatives, as well as heparan sulphate and dermatan sulphate, which, however, have the disadvantage, due to their origin, of being very expensive.

In particular, it is known that dermatan sulphate is a family of polymers with a variable degree of polymerisation, formed of repeating units consisting of a uronic acid group (iduronyl or glucuronyl) and of an acetyl 4-sulphated galactosaminyl group (H. W. Stuhlsatz, "The Methodology of Connective Tissue Research", (1976), 137–146). Natural dermatan sulphate has a molecular mass of between $2 \times 10^4$ and $4 \times 10^4$ D. This product is particularly advantageous as an anticoagulant and antithrombin (F. Fernandez et al., British Journal of Haematology, (1986), 64, 309–317).

Moreover, it is known (I. Bjbrk and U. Lindahl, "Molecular and Cellular Biochemistry", (1982), Publishers Dr. W. Junk—Netherlands) that blood clotting is a complex physiological phenomenon whose mechanism can be schematised and summarised in the following way:

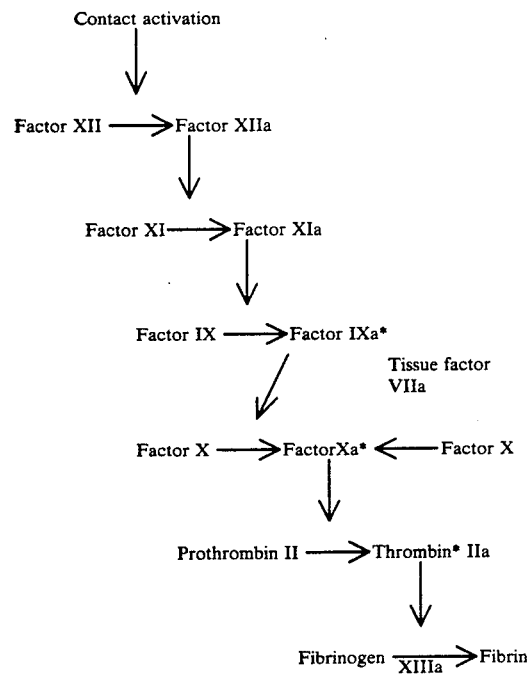

Certain stimuli, such as contact activation and tissue factors, trigger off the successive activation of a series of clotting factors present in the blood plasma, these being marked by Roman numerals in the above scheme and the presence of the suffix a denoting the activated (suffix a present) or inactivated (suffix a absent) form of a given clotting factor.

Whatever the nature of the stimulus, the final stages are identical: factor Xa activates factor II (also called prothrombin) which, in its activated form (factor IIa, also called thrombin), causes the partial proteolysis of soluble fibrinogen with release of insoluble fibrin, which is the main constituent of the blood clot.

Under normal physiological conditions, regulating proteins such as antithrombin III (ATIII) and heparin cofactor II (HCII) are also present in the plasma.

Antithrombin III exerts an inhibiting activity on all the clotting factors marked by an asterisk (*) in the above scheme. This inhibition is very strongly accentuated in the presence of heparin or of synthetic oligosaccharides of the heparin type (D. H. Atha et al., Biochemistry, (1985), 24, 6723–6729).

Heparin cofactor II exerts an inhibiting activity only on factor IIa (thrombin), which catalyses the last stage of clotting. This activity is accentuated significantly in the presence of heparin or of dermatan sulphate (D. M. Tollefsen, J. Biol. Chem, (1983), 258, 6713–6716).

The inhibition of factor Xa or of factor IIa constitutes a favoured means for obtaining an antilo coagulating and antithrombotic activity since these two factors take part in the last two stages of clotting, which are independent of the triggering stimulus.

In order to obtain inhibition of factor IIa alone, a particularly advantageous possibility consists in taking advantage of the specificity of heparin cofactor II and in seeking to accentuate its inhibiting activity. Dermatan sulphate is the known product possessing the most powerful accentuating activity of this type.

It is also known that the main heparin chain is constructed in two stages. In a first stage, heparin is biosynthesised from a precursor proteoglycan whose polysaccharide part consists of a family of polymers with a variable degree of polymerisation formed from repeating β-D-glucuronyl-1,4-α-N-acetyl-D-glucosaminyl-(1,4) disaccharide units. This polysaccharide part is generally called N-acetylheparosan (J. Navia, Anal. Biochem., (1983), 135, 134–140). This first stage of biosynthesis is the only time when it is truly possible to speak of a "disaccharide unit" because the second stage of the biosynthesis will profoundly change this simple skeleton ("L'héparine, fabrication, structure, propriétés, analyses", J. P. Duclos, (1984) pp. 81–83, Masson Ed.—France).

Indeed, natural heparin resulting from biosynthesis is a polysaccharide consisting of molecules of glucuronic acid and of iduronic acid (uronic acids), optionally sulphated in position 2, combined with molecules of glucosamine, optionally sulphated in position 6 and sulphated or acetylated on the amine in position 2.

It is also known that certain bacteria of the species *Escherichia coli* produce a capsular polysaccharide, generally called antigen K5, which is a family of polymers consisting of repeating β-D-glucuronyl-1,4-α-N-acetyl-D-glucosaminyl-(1,4) units, (W. F. Vann et al., Eur. J. Biochem., (1981), 116, 359–364).

This polysaccharide, which is of the same chemical nature as the polysaccharide part of the precursor proteoglycan of heparin, will here be called N-acetylheparosan. This product has a molecular mass between $10^5$ and $2.0 \times 10^6$ D and, in the "uronic acid" units, a very regular structure composed solely of D-glucuronic acid (W. F. Vann et al., Eur. J. Biochem., (1981), 116, 359–364, and patent application EP-A-0,333,243).

Patent application EP-A-0,333,243 describes the O-sulphated polysaccharide K5 (O-sulphated N-acetylheparosan) as well as certain of its cleavage products, composed respectively of 4, 6 or 8 "sugar" units, also O-sulphated. These products have an antiangiogenic and antitumour activity, with a favourable ratio of these activities with respect to the anticoagulating properties. This document also describes cleavage products of N-acetylheparosan composed respectively of 4, 6, 8 or 10 "sugar" units, and also high molecular mass O-sulphated N-acetylheparosans. These last products, subjected to a drastic depolymerisation according to the method described by W. F. Vann et al. in Eur. J. Biochem., (1981), 116, 359–364 give small cleavage products of O-sulphated N-acetylheparosans consisting of 8, 6 or 4 "sugar" units as described in patent EP-A-0,333,243.

Patent application EP-A-0,333,243 also describes the preparation of a pentasaccharide having the O-sulphated N-acetylheparosan structure by total chemical synthesis.

It is also known that the polysaccharide K5, when N-deacetylated and N-sulphated, can be used as a substrate for enzymes which catalyse the last modification reactions of the polymer, namely hexuronosyl C5-epimerisation and O-sulphation in the biosynthesis of heparin (M. Kusche et al., Biochem. J. (1991), 275, 151–158). M. Kusche et al. describe the preparation of the N-deacetylated, N-sulphated polysaccharide K5 by N-deacetylation using hydrazine/hydrazine sulphate and N-sulphation by treatment of the N-deacetylated product with the trimethylamine/sulphur trioxide complex.

Finally, it is known that, by partial 5-epimerisation and O-sulphation of the C5-epimerised, N-deacetylated and N-sulphated polysaccharide K5, products are obtained which have an anti-Xa activity and an anti-IIa activity via HCII which lies between that typical of mucous heparin and that of heparan sulphate (B. Casu et al., International Symposium on Heparin and Related Polysaccharides, Uppsala, 2–6 September, 1991, Abstract No. 12). All these products, like heparin, have, in their chains, both glucuronic structures and iduronic structures. C5-Epimerised, N-deacetylated and N-sulphated derivatives of the polysaccharide K5, containing in their chains both glucuronic structures and iduronic structures, are also described by M. Kusche et al., Biochem. J. (1991), 275, 151–158.

J. Riesenfeld et al. (Glycoconjugate (1987), 4, 179–189) describe, during a study intended to elucidate the biosynthesis of heparin, the sulphation of an N-acetylheparosan by an enzyme without mentioning the exact structure of the products obtained.

Moreover, it is known that French Patent No. 2,584,728 of the Oct. 11, 1987 (corresponding to the application FR-85.10787) describes a process for the sulphation of glycosaminoglycans, and especially of heparin, which makes it possible to introduce sulphuric ester groups ($-SO_3^-$ group) in place of primary hydroxyl ($-OH$) groups on the saccharide units of the starting glycosaminoglycan without changing its degree of polymerisation or its homogeneity.

It has now been found that, by O-sulphation of the N-deacetylated and N-sulphated polysaccharide K5, a high molecular mass N,O-sulphated heparosan is obtained which has a good activity towards clotting, the said activity manifesting itself via heparin cofactor II and, which is surprising, via antithrombin III. More particularly, it has been found, in an unexpected way, that partial 5-epimerisation is not necessary and that the N,O-sulphated heparosans, which contain in their chains, beside the glucosamine units, solely glucuronic units, can be used as active principles of anticoagulating and antithrombotic medicines.

The high molecular mass N,O-sulphated heparosans which are the subject of the present invention are therefore distinguished from other products already described in the literature by their novel structure, especially characterised by a high degree of sulphation (sulphation also on the amine group of the glucosamine), by the absence of iduronic Acid and by their unexpected pharmacological properties. They have an anticoagulating activity with respect to heparin cofactor II (HCII) which is stronger than that of dermatan sulphate. Indeed, their pharmacological activities are comparable to those of the glycosaminoglycans commonly used in therapeutics, especially those of heparin, and can be used for the control of clotting. The products of the invention more particularly find their applications as antithrombins.

The expression "high molecular mass", as used in the present description for polysaccharide K5 and for its N-deacetylated and N-sulphated derivatives as well as for the N,O-sulphated heparosans which are the subject of the present invention, refers to a molecular mass greater than $1.5 \times 10^4$ D, namely beyond the limit within which the said molecular mass is determined with some precision according to standard analytical methods. When reference is made to the natural polysaccharide K5 and to its derivatives, it is understood that their molecular mass is that shown in the above references W. F. Vann et al. (Eur. J. Biochem., (1981), 116, 359–364) and EP-A-0,333,243, unless otherwise specified. However, the same expression also includes products which have a molecular mass lower than that of the natural polysaccharide K5, obtained by splitting and/or cleaving and formed of chains with a molecular mass of between $1.5 \times 10^4$ and $10^5$ D. In fact, the expression "high molecular mass" is applied to any, optionally N-deacetylated and N-sulphated, product of polysaccharide K5 type, including the cleavage products, or to any N,O-sulphated heparosan, including its cleavage products, which has a molecular mass in the range between approximately $1.5 \times 10^4$ and approximately $4.0 \times 10^6$ D.

The subject of the present invention is N,O-sulphated heparosans consisting of chains or of a mixture of chains having a molecular mass of between $1.5 \times 10^4$ and $4.0 \times 10^6$ D, characterised by a repeating disaccharide structure of formula I:

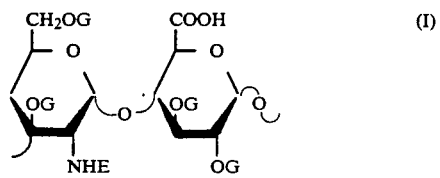

in which

E represents, in 0 to 80 % of the disaccharide units of the said N,O-sulphated heparosans, an acetyl group and, in the remaining disaccharide units, a sulphate group and optionally a hydrogen atom, G represents a hydrogen atom and a sulphate group, and the pharmaceutically acceptable salts of the said N,O-sulphated heparosans.

The degree of sulphation of the high molecular mass N,O-sulphated heparosans, expressed as sulphate/carboxyl ratio, is preferably from 1.5 to 3.0.

The invention also relates to an N,O-sulphated heparosan composition containing at least 70% by mass of an N,O-sulphated heparosan which is described above and is the subject of the present invention.

The N,O-sulphated heparosans which are the subject of the present invention can consist of identical polysaccharide chains of well-defined molecular mass, this molecular mass being in the range from $1.5 \times 10^4$ to $4.0 \times 10^6$ D. They can also consist of a mixture of chains of variable molecular masses, these molecular masses being between $1.5 \times 10^4$ and $4.0 \times 10^6$ D. The spread in the molecular masses of these chains can be more or less significant. Indeed, the N,O-sulphated heparosans which are the subject of the present invention can consist of chains having a molecular mass difference between themselves of at most approximately $3.9 \times 10^6$ D or, on the contrary, only of chains having a molecular mass difference themselves of approximately 300 D, which corresponds to a unit of uronic structure (D-glucuronic acid or its derivatives) or of glucosamine structure, or else of chains having a molecular mass difference between themselves which is less than 300 D in the case where the N,O-sulphated heparosans result from a chemical cleaving. It is also obvious that, according to the composition of each N,O-sulphated heparosan, the molecular mass of the chains having either the lowest molecular mass or the highest molecular mass can correspond to any value between $1.5 \times 10^4$ and $4.0 \times 10^6$ D. The term "approximately" indicates molecular weights very close to the stated values and it is used in order not to be limited to these specific values. This is justified by the difficulties encountered during the evaluation of the molecular weights and by the spread in the results which those skilled in the art can obtain, due to the precision of the methods used, however effective the latter may be.

The expression "G represents a hydrogen atom and a sulphate group" used above indicates that G in the disaccharide unit of formula I represents, for certain positions, a hydrogen atom and, in the other remaining positions, a sulphate group. In the same way, E represents, in certain disaccharide units, an acetyl group and, in the remainder of these units, a sulphate group or optionally a hydrogen atom. The disaccharide units of the N,O-sulphated heparosans can thus not all be identical.

Formula I represents a repeating disaccharide structure formed from a glucosamine unit and a D-glucuronic acid unit. The said units can be reversed, more particularly, if it is considered that the disaccharide structure of formula I is repeated n times and that the nonreducing unit of the chains can be equally well either a glucosamine unit, such as represented in formula I with an hydroxyl group in position 4, this glucosamine unit being sulphated or nonsulphated, or a D-glucuronic acid optionally containing a double bond in position C4-C5 and being sulphated or nonsulphated. The reducing unit can be equally well either a D-glucuronic acid, such as represented in formula I, substituted with a hydrogen on the anomeric oxygen, or a glucosamine.

The preferred compounds of the invention consist of chains whose reducing and nonreducing ends are sulphated or nonsulphated uronic units, sulphated or nonsulphated glucosamine or sulphated or nonsulphated N-acetylglucosamine.

As in the case of heparin, and except when otherwise indicated, the terms "Polysaccharide K5" and "N,O-sulphated heparosan" referred to the products mean the products in the form of sodium salts.

According to another of its aspects, a subject of the present invention is a process for the preparation of high molecular mass N,O-sulphated heparosans, characterised in that:

(i) either a starting material, consisting of an N-deacetylated, N-sulphated polysaccharide K5, or one of its cleavage products, is subjected to an O-sulphation, (ii) or a starting material consisting of an N-deacetylated polysaccharide K5, or one of its cleavage products, is subjected to a partial N,O-sulphation optionally followed by a complete N-sulphation, the product thus obtained is then isolated and is optionally converted to a pharmaceutically acceptable salt.

As starting materials, substances are used which have a molecular mass in the range from approximately $1.0 \times 10^4$ to approximately $2.0 \times 10^6$ D, in order to prepare N,O-sulphated heparosans which are the subject of the present invention. N,O-Sulphated heparosans having a molecular mass of approximately $4.0 \times 10^6$ D are obtained from substances having a molecular mass of approximately $2.0 \times 10^6$ D. The mass difference shown between the starting materials and the N,O-sulphated heparosans is due to N,O-sulphation.

More particularly, another subject of the present invention is a process for the preparation of a composition containing 70% to 100% of a high molecular mass N,O-sulphated heparosan which is the subject of the present invention, characterised in that it comprises the sequence of the following stages:

stage a: culturing of a strain of *Escherichia coli* (K5) to form a high molecular mass N-acetylheparosan (polysaccharide K5), stage b: isolation and purification of the N-acetylheparosan formed in order to obtain a composition containing 70% to 100% of a N-acetylheparosan consisting of a mixture of chains having a molecular mass of between $1.0 \times 10^4$ and $2.0 \times 10^6$ D, characterised by a repeating disaccharide structure of formula II:

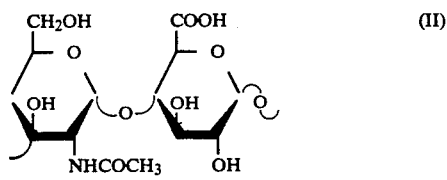

stage c: deacetylation of this N-acetylheparosan composition in order to obtain a composition containing 70% to 100% of a heparosan consisting of a mixture of chains having a molecular mass of between $1.0 \times 10^4$ and $2.0 \times 10^6$ D, characterised by a repeating disaccharide structure of formula III:

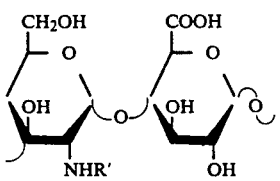

(III)

in which R' represents, in 0 to 80% of the disaccharide units, an acetyl group and, in the remaining disaccharide units, a hydrogen atom, stage d:
either a complete or partial N-sulphation in order to obtain a composition containing 70% to 100% of an N-sulphated heparosan consisting of a mixture of chains having a molecular mass of between $1.0 \times 10^4$ and $2.0 \times 10^6$ D, characterised by a repeating disaccharide structure of formula IV:

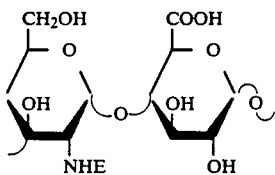

(IV)

in which E represents, in 0 to 80% of the disaccharide units, an acetyl group and, in the remaining disaccharide units, a sulphate group and optionally a hydrogen atom, this partial or complete N-sulphation stage being followed by a partial or complete O-sulphation stage,
or a partial N,O-sulphation of this heparosan composition,
or a partial N,O-sulphation of this heparosan composition followed by a complete N-sulphation stage,
and optionally contains one or more stages, carried out at the end of stages a, b, c and d, in which the molecular masses are split.

It is possible to use, as starting material, an N-deacetylated, N-sulphated polysaccharide K5 such as that described by M. Kusche et al. (Biochem. J. (1991), 275, 151–158).

Another advantageous starting material is a polysaccharide K5 such as described in EP-A-0,333,243.

A particularly advantageous starting material is a polysaccharide K5 obtained by culturing *Escherichia coli* SEBR 3282. This is a strain derived from the strain Bi 8337-41 (O10:K5:H4) ATCC 23506 (described especially by D. S. Gupta et al.; FEMS Microbiology Letters, (1982), 14, 75–78 and W. Vann, Eur. J. Biochem., (1981), 116, 359–364).

*E. coli* strain SEBR 3282 has been deposited under the terms of the Budapest Treaty with the CNCM of the Pasteur Institute, Paris, France, under Accession No. I-1013. During the pendency of this application, access to the deposit will be afforded to one determined by the Commissioner of the Patent and Trademark Office to be entitled thereto. All restrictions imposed by the depositor on the availability to the public of the deposited material will be irrevocably removed upon the granting of a patent. The deposit will be maintained for a term of at least 30 years and at least 5 years after the most recent request for the furnishing of a sample of the deposited material.

The strain *Escherichia coli* SEBR 3282 responds positively to the typing test by the K5 specific phage, according to the method of B. Kaiser et al., (J. Clin. Microbiol., (1984), 19, 2, 264–266). It is therefore certainly an *Escherichia coli* (K5) strain. This strain was deposited with the CNCM at the Pasteur Institute, Paris, France, under No. I-1013. It is also possible to use a mutant, either spontaneous or induced, of this strain as well as other suitable strains of *Escherichia coli* (K5), for example the strain Bi 626–42 (O12:K5(L):NM) ATCC 23508.

A culture medium rich in glycerol, in preference to glucose is used for the preparation of a high molecular mass N-acetylheparosan used as starting material for the chemical semisynthesis of the products of the invention.

Culturing of the strain of *Escherichia coli* (K5) is preferably continued for at least two hours after growth of the biomass has stopped (aged approximately 25–35 hours in the fermenter).

In stage b, the isolation and the purification of the N-acetylheparosan, in order to obtain a composition containing 70% to 100% of an N-acetylheparosan consisting of a mixture of chains having a molecular mass of between $1.0 \times 10^4$ and $2.0 \times 10^6$ D, characterised by a repeating disaccharide structure of formula II, are carried out by a process comprising at least one precipitation stage and one ion exchange chromatography stage. This last stage is carried out by preferably using a Q-Sepharose column or an equivalent column. Precipitation is carried out with a suitable organic solvent and especially an alcohol, preferably ethanol. During this process, the N-acetylheparosan can be in the form of a salt, preferably in the form of the sodium salt.

By way of example, the preferred process for isolation and purification can be schematised as follows:
stage $a_1$: Precipitation with ethanol,
stage $b_1$: Dialysis,
stage $c_1$: Precipitation with ethanol, then dehydration and drying,
stage $d_1$: Purification by anion exchange chromatography,
stage $e_1$: Precipitation, with ethanol, of the eluate obtained in stage $d_1$, dehydration, drying and grinding.

As regards stages $a_1$, $b_1$ and $c_1$, the order in which they are carried out is of little importance. One of the stages $a_1$ or $c_1$ can be omitted.

In stage $e_1$, precipitation with ethanol is not absolutely necessary. It is possible to isolate the N-acetylheparosan by other methods such as, for example, by evaporation under vacuum of the eluate obtained in stage $d_1$.

The isolation and the purification of the N-acetylheparosan, in order to obtain a composition containing 70% to 100% of an N-acetylheparosan consisting of a mixture of chains having a molecular mass of between approximately $1.5 \times 10^4$ and $2.0 \times 10^6$ D, can also be carried out in the following way:
stage $a'_1$: Dialysis,
stage $b'_1$: Purification in acidic medium and removal of the impurities which are insoluble in aqueous solutions of pH 3.5 and pH 1.8,
stage $c'_1$: Precipitation with ethanol, then dehydration and drying,
stage $d'_1$: Alkaline hydrolysis and dialysis,
stage $e'_1$: Purification by anion exchange chromatography, stage f'₁: Purification by exclusion chromatography.

This isolation and purification process is also a preferred process of the invention.

Alkaline hydrolysis is carried out with a solution of NAOH at a temperature between 30° C. and 80° C.

By applying the isolation and purification processes, it is possible to use as starting material either the suspension obtained at the end of culturing, in which case a prior filtration is necessary, or a substance which has already been subjected to a preliminary purification carried out according to a process which comprises the following stages:

stage a"₁: Centrifuging the suspension obtained at the end of culturing, stage b"₁: Bringing the supernatant into contact with an alkaline solution, stage c"₁: Prefiltration, stage d"₁: Concentration on a membrane with a predetermined threshold cutoff value, and optionally, stage e"₁: Dialysis.

It is also possible here to use, as alkaline solution, a solution of NAOH.

Preferably, a preliminary purification of the product obtained at the end of culturing is carried out, according to the method described above.

The two ends, reducing and nonreducing, of the N-acetylheparosans of formula II, such as obtained according to the process described above and using the strain *Escherichia coli* SEBR 3282 or another suitable strain as indicated above, are uronic units or N-acetylglucosamine.

In the majority of chains, the nonreducing end is a uronic unit of formula (a):

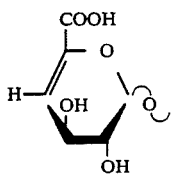
(a)

The optional enrichment of the composition obtained in N-acetylheparosan, consisting of a mixture of chains having a molecular mass of between $1.5 \times 10^4$ and $2.0 \times 10^6$ D and having a repeating disaccharide structure of formula II, can be carried out to varying degrees and especially up to isolation of the said N-acetylheparosan. The enrichment is produced by using conventional techniques for fractionating molecular masses, such as gel permeation chromatography and ultrafiltration (A. A. Horner, Biochem. J., (1989), 262, 953–958; G. Pyler et al., J. Biol. Chem. (1988), 263, 11, 5197–5201 and U. Lindahl et al., J. Biol. Chem. , (1984) , 259, 20, 12368–12376) . It is also possible to use the method of ethanolic fractionation (Patent Application EP-A-0,287,477). This last fractionation method is particularly valued among other conceivable methods.

In stage c, the partial deacetylation of the compositions containing 70% to 100% of N-acetylheparosan, which produces compositions containing 70% to 100% of a high molecular mass heparosan, consisting of a mixture of chains having a molecular mass of between $1.0 \times 10^4$ and $2.0 \times 10^6$ D, characterised by a repeating disaccharide structure of formula III indicated above, is carried out by treatment with a deacetylating agent.

Deacetylating agents which may be mentioned are phosphorus pentasulphide, triethyloxonium fluoroborate, sodium hydroxide or hydrazine, the last two agents being particularly valued. It is also possible to use strong inorganic acids, such as hydrochloric acid, sulphuric acid, and the like. The length of the reaction depends on the operating conditions chosen and especially on the temperature and concentration of the deacetylating agent in the reaction medium.

The enrichment of the composition of heparosan in heparosan consisting of a mixture of chains having a molecular mass of between $1.0 \times 10^4$ and $2.0 \times 10^6$ D, characterised by a repeating disaccharide structure of formula III, is carried out by using conventional techniques for the fractionation of the molecular masses mentioned above (gel permeation chromatography, ultralo filtration and fractionation by water-miscible organic solvents and especially ethanolic fractionation) . In this case, it is possible to obtain compositions containing 90% to 100% by mass of a heparosan consisting of a mixture having a molecular mass of between $1.0 \times 10^4$ and $2.0 \times 10^6$ D and having the repeating disaccharide structure of formula III.

According to the first variation of stage d (partial or complete N-sulphation followed by a partial or complete O-sulphation), the N-sulphation is carried out according to known methods (M. Kusche et al., Biochem. J. (1991) 275, 151–158). More precisely, the N-sulphation is carried out using a complex of sulphur trioxide with an organic base such as trimethylamine, triethylamine or pyridine. It can also be carried out with chlorosulphonic acid in solution in pyridine. The complex of sulphur trioxide ($SO_3$) with trimethylamine is advantageously used and the N-sulphation reaction is carried out at a temperature between 20° C. and 80° C. in aqueous alkaline medium. At the end of the N-sulphation reaction, the product thus obtained is precipitated by addition of a suitable quantity of ethanol. The precipitate formed is taken up in ultrapurified water, dialysed against the latter, lyophilised and dried. This purification procedure is given by way of example and does not exclude equivalent processes. The purification stages can be repeated several times.

Subsequently, and according to the process of the invention, before the O-sulphation stage, the N-sulphated heparosan is preferably converted to a salt of an organic base or to a quaternary ammonium salt. Tetrabutylanunonium hydroxide is preferably used to form the quaternary ammonium salt.

The O-sulphation reaction is carried out in formamide or another, chemically equivalent solvent, using, for example, a complex of sulphur trioxide with an organic base such as trimethylamine, triethylamine or pyridine or even using chlorosulphonic acid in the presence of pyridine. A sulphur trioxide/pyridine complex is preferably used. The O-sulphation reaction is generally carried out at a temperature between 10° C. and 50° C.

The N,O-sulphated heparosan is then precipitated by adding sodium chloride to the reaction medium until a 0.3M to 0.5M NaCl solution is obtained and then a suitable quantity of ethanol. Purification of the composition of the N,O-sulphated heparosan is then carried out in the following way: the precipitate is taken up in a solution of 0.3M to 0.5M NaCl, it is reprecipitated with ethanol, the precipitate formed is isolated, taken up in ultra-purified water, dialysed against the latter and optionally lyophilised and dried.

The purification procedure mentioned above is given by way of example and does not exclude equivalent processes. The purification can be carried out once or more than once.

The enrichment of the N,O-sulphated heparosan composition in N,O-sulphated heparosan having a desired molecular mass is carried out using conventional techniques, already mentioned, for the fractionation of molecular masses. It is advantageous to carry out this enrichment.

According to the second and the third variation of stage d of the process (partial N,O-sulphation of the heparosan composition or partial N,O-sulphation followed by a complete N-sulphation stage), before the partial N,O-sulphation stage, the heparosans can be converted to a salt of an organic base or to a quaternary ammonium salt. Tetrabutylammonium hydroxide is preferably used to form the quaternary ammonium salt of the heparosans.

The partial N,O-sulphation stage, carried out according to the process described in French Patent No. 2,584,728 of the Oct. 11, 1987 (corresponding to the application FR-85.10787), is carried out in a polar aprotic solvent, such as dimethylformamide, dimethyl sulphoxide, hexamethylphosphoramide or acetonitrile or a mixture of these solvents, using, for example, a complex of sulphur trioxide with an organic base, such as trimethylamine, triethylamine or pyridine. It can also be carried out with chlorosulphonic acid in solution in pyridine. The sulphur trioxide/pyridine complex is preferably used.

It is also possible to use other sulphation agents, especially those which are reported by E. E. Gilbert in Chemical Review, (1962), 62, 549–589. The N,O-sulphation reaction is generally carried out at a temperature between 0° C. and 100° C., preferably between 10° C. and 50° C., and for a time of between 6 h and 14 h.

During the preparation process, at the end of the partial N,O-sulphation reaction, the N,O-sulphated heparosan composition containing 70% to 100% of an N,O-sulphated heparosan, which is the subject of the present invention, is precipitated by addition of sodium chloride, until a 0.3M to 0.5M sodium chloride solution is obtained, and then of a suitable quantity of ethanol. The precipitate formed is taken up in a 0.3M to 0.5M sodium chloride solution. This solution is then neutralised. After addition of a suitable quantity of ethanol, the precipitate formed is isolated, taken up in ultrapurified water, dialysed against the latter, lyophilised and dried.

The N,O-sulphation stage, as well as the N,O-sulphated heparosan composition purification stages described in the above paragraph, can be repeated once or more than once. Here also, the purification procedure is given by way of example and does not exclude equivalent processes.

This N,O-sulphation stage is preferably followed by a complete N-sulphation stage, generally carried out in an aqueous solvent, advantageously of basic pH, with a sulphation agent, such as a complex of sulphur trioxide with an organic base, for example trimethylamine, according to the N-sulphation technique mentioned above.

At the end of the complete N-sulphation stage, the N,O-sulphated heparosan composition is precipitated after addition of sodium chloride, until a 0.3M to 0.5M sodium chloride solution is obtained, and of ethanol. The precipitate formed is then redissolved in a 0.3M to 0.5M sodium chloride solution, reprecipitated with ethanol, then taken up in ultrapurified water, dialysed against the latter, lyophilised and dried.

As has already been mentioned, it is advantageous to carry out an enrichment of the N,O-sulphated heparosan composition in N,O-sulphated hephrosan. This is carried out using conventional techniques for the fractionation of molecular masses.

The N,O-sulphated heparosans, which are the subject of the present invention, and the N,O-sulphated heparosan compositions containing at least 70% of a novel N,O-sulphated heparosan, which are the subject of the present invention, are advantageously obtained either by a process comprising a final N-sulphation reaction or by a process comprising first an N-sulphation followed by a partial or complete O-sulphation. E then represents, for the repeating structures in formula (I), the acetyl group and the sulphate group.

It is estimated that the N,O-sulphated heparosans, which are the subject of the present invention, contain less than 0.2 $\mu$mol/mg of free amino group ($NH_2$).

The acetyl group of the disaccharide units is preferably present at a level less than or equal to 60% and it is estimated that the degree of sulphation, expressed as the sulphate/carboxyl ratio, is between 1.5 and 3.0.

The preferred products of the invention are the N,O-sulphated heparosans consisting of at least 70% by mass of chains having a molecular mass of between $1.0 \times 10^5$ and $5.0 \times 10^5$ D, as well as the N,O-sulphated heparosans consisting of at least 70% by mass of chains having a molecular mass of between $2.5 \times 10^4$ and $2.5 \times 10^5$ D.

There may be cited, as other preferred products of the invention, the N,O-sulphated heparosans consisting of at least 70% by mass of chains having a molecular mass of between $2.0 \times 10^4$ and $10^5$ D.

The process for preparing the N,O-sulphated heparosans described above, as well as the purification methods, make it possible to obtain the N,O-sulphated heparosans in the form of sodium salts. It is possible to obtain from these salts, by applying the methods used to prepare the various salts of heparin or of nonsalified heparin ("L'héparine, fabrication, structure, propriétés, analyses", J. P. Duclos, (1984) pp. 81–83, Masson Ed. —France), either other salts of N,O-sulphated heparosans or nonsalified N,O-sulphated heparosans. Salts of N,O-sulphated heparosans means all the pharmaceutically acceptable salts. These salts are obtained by conventional methods described especially for the preparation of the salts of heparin (U.S. Pat. No. 4,168,377).

The N,O-sulphated heparosans, which are the subject of the present invention, have advantageous pharmacological and biochemical properties which are altogether surprising in relation to the teachings of the prior art. In particular, in contrast to the sulphated products of K5 antigen described in the patent EP-A-0,333,243, which have an antiangiogenic and antitumor activity or else even an activity against enveloped viruses, with a favourable ratio of these activities with respect to the anticoagulating properties, the N,O-sulphated heparosans of the present invention have a good regulating activity for clotting. This activity is much greater than that of dermatan sulphate on the various clotting parameters and it is more comparable with that of heparin.

More particularly, the ATIII- or HCII- dependent anti-IIa activity of representative products of the invention was determined according to the methods described by D. Dupouy et al. in Thrombosis and Haemostasis, (1988), 60, 2, 236–239, for heparin cofactor II (HCII) and by M. L. Larsen et al. in Thrombosis Research, (1978), 13, 2, 285–288 for antithrombin (ATIII).

In both cases, the test consists in measuring the in vitro inhibiting effect of the product studied on purified thrombin (factor IIa) in the presence of purified HCII or ATIII in determining the amidolytic activity of thrombin, with respect to a chromogenic substrate. As it has the strongest HCII-dependent anti-IIa activity, dermatan sulphate, prepared according to the method described by H. W. Stuhlsatz et al. in "The Methodology of Connective Tissue Research", (1976) 137–146, is used as reference substance in the measurement test of this activity, the result being expressed in mg of dermatan sulphate (DS) equivalents in activity to 1 mg of the studied product (mg DS equiv/mg).

The anti-Xa activity (Yin-Wessler titre) of the said representative products of the invention was measured by the method described by E. T. Yin et al. in J. Lab. Clin. Med. (1973), 81, 2, 298–310, whereas their overall anticoagulating activity was measured according to the APTT test described by R. R. Proctor et al. in Am. J. Clin. Path. (1961), 36, 212–219. All the products tested showed an HCII-dependent anti-IIa activity which was markedly greater than that of dermatan sulphate. The ATIII-dependent anti-IIa activity and the Yin-Wessler titre, although lower than those of the heparins, are shown to be greater than those of dermatan sulphate. Their APTT titre is approximately 2 to approximately 15 times greater than that of dermatan sulphate, and can reach 40% of that of heparin.

The N,O-sulphated heparosans of the invention thus have a particularly advantageous specificity of action and anticoagulating activity.

The N,O-sulphated heparosans of the present invention have very low toxicity; their toxicity is perfectly compatible with their use as medicines.

The invention thus also extends to the pharmaceutical compositions containing, as active principle, an N,O-sulphated heparosan, which is the subject of the present invention, one of its salts, or an N,O-sulphated heparosan composition containing at least 70% of this N,O-sulphated heparosan or one of its salts, in combination with one or more suitable pharmaceutical vehicles.

These pharmaceutical compositions are useful especially for the treatment, preventative or curative, of disorders of the vascular wall, such as atherosclerosis and arteriosclerosis, and hypercoagulability states observed, for example, following surgical operations, tumour growths or clotting disorders induced by enzymatic, bacterial or viral activators.

The dosage can vary widely as a function of the age, weight and state of health of the patient, and of the nature and the severity of the ailment, as well as of the administration route. This dosage comprises the administration either of one or more doses of approximately 1 mg to 1 g per day, preferably of approximately 5 mg to 500 mg per day, for example of the order of 200 mg per day, intravenously or subcutaneously, administered noncontinuously or at regular intervals, or of a daily dose of the order of 200 mg to 1000 mg per day orally.

These doses can naturally be adjusted for each patient according to the results observed and the blood analyses previously carried out.

The N-acetylheparosans (compounds of formula II), the heparosans (compounds of formula III) and the N-sulphated heparosans (compounds of formula IV) resulting respectively from stages b, c and d in the preparation of the starting materials of the process of the present invention, the N,O-sulphated heparosans which are the subject of the present invention, as well as the cleavage products of all these substances, constitute high molecular mass intermediates useful for the preparation, by depolymerisation, of low molecular weight N-acetylheparosans, heparosans, N-sulphated heparosans and N,O-sulphated heparosans, i.e. lower than $1.5 \times 10^4$ D and especially between $1.5 \times 10^3$ and $1.5 \times 10^4$ D.

The depolymerisation can be carried out according to the methods described in the literature for preparing low molecular weight heparins, for example, by periodate depolymerisation and especially according to the method described in the patent application EP-0,287,477, or by free radical depolymerisation and especially according to the method described in the patent EP-0,121,067. Depolymerisation can also be carried out by β-elimination and more particularly according to the method described in the patent application EP-0,040,144. In this case, an optionally O-sulphated, α,β-unsaturated uronic acid ending of formula (a) is obtained at the nonreducing end.

Depolymerisation by reacting nitrous acid, and especially that described in Patent EP-0,037,319, is also preferentially used as the depolymerisation method. This method leads, in a first step, to products having, at the reducing end, a 2,5-anhydromannose unit of formula (b):

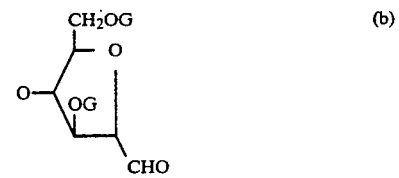

in which G represents a hydrogen atom or a hydrogen atom and a sulphate group, according to the substances used during depolymerisation (G is a hydrogen atom for the compounds of formulae III and IV and G is a hydrogen atom and a sulphate group for the substances of formula I), and then, when the depolymerisation is followed by a reduction, cleavage products are obtained which have, at the reducing end, a 2,5-anhydromannitol unit of formula (c):

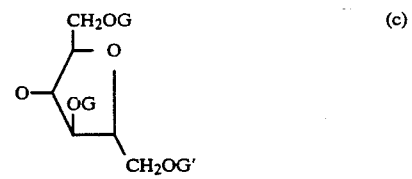

in which G' represents a hydrogen atom when the depolymerisation is not followed by sulphation or a sulphate group when the depolymerisation is followed by a sulphation.

When depolymerisation by reacting with nitrous acid is followed by an oxidation, cleavage products are obtained which have, at the reducing end, a 2,5-anhydromannonic acid unit of formula (d):

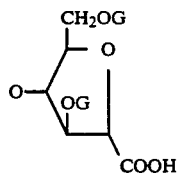

(d)

Depolymerisation can also optionally be carried out by enzymatic methods such as, for example, those shown in Patent Applications EP-0,244,235 and EP-0,244,236.

The depolymerisation methods shown above are given by way of examples and are not limiting. It is possible to use any other method for depolymerisation of glycosaminoglycans. Subsequently, the depolymerisation products can be subjected to one or more fractionations in order to obtain N-acetylheparosans, heparosans, N-sulphated heparosans and N,O-sulphated heparosans consisting of low molecular mass chains.

Another subject of the present invention is the employment of high molecular mass N-acetylheparosans (compounds of formula II), heparosans (compounds of formula III), N-sulphated heparosans (compounds of formula IV), as well as the high molecular mass N,O-sulphated heparosans (compounds of formula I), which are the subject of the present invention, in order to obtain, after depolymerisation, low molecular mass N-acetylheparosans, heparosans, N-sulphated heparosans and N,O-sulphated heparosans of less than $1.5 \times 10^4$ D.

Another, more particular subject of the present invention is the employment of N-sulphated heparosans (compounds of formula IV) and N,O-sulphated heparosans (compounds of formula I) for the preparation, after cleavage, of low molecular mass N,O-sulphated heparosans of less than $1.5 \times 10^4$ D and especially of between $1.5 \times 10^3$ D and $1.5 \times 10^4$ D.

When compounds of formula IV are used, during the cleavage, as starting materials, low molecular mass N,O-sulphated heparosans are obtained by subjecting the low molecular mass N-sulphated heparosans obtained via the cleavage of the products of formula IV either to a partial N,O-sulphation or to a partial N,O-sulphation followed by a complete N-sulphation stage.

The invention is illustrated by the examples below.

PREPARATIONS

Preparation I

Preparation of a High Molecular Mass N-acetylheparosan (Process I)

1) Culturing of the bacterial strain *Escherichia coli* (K5) and separation of a filtrate containing N-acetylheparosan 400 ml of medium B, of composition specified in Table 1 below, is cultured with the strain *Escherichia coli* SEBR 3282 (deposited with the CNCM at the Pasteur Institute, Paris, France, under No. I-1013) and the mixture is incubated with stirring for 2 h at 37° C.

The preculture obtained is then transferred into an 18.5-1 fermenter containing 11 l of medium A, of composition specified in Table I below, and the mixture is incubated for 6 h 30 min at 37° C. and at a pH of 7.2, the oxygen partial pressure being maintained at 40 mm Hg by adjusting the injection of air (up to 20 l/min) and the stirring. Glycerol is then added by continuously introducing a sterile solution containing 500 g/l of glycerol at the rate of 18 g/h for 16–17 h.

Culturing is continued under the same temperature, pH and oxygen partial pressure conditions until virtually all the glycerol has been consumed. Monitoring the DO ($\lambda = 600$ nm) of the culture suspension medium after completion of the glycerol addition shows a stationary state or slight lysis until culturing is stopped after 28–30 h in the fermenter.

The culture broth is then cooled to 25° C. and is then filtered through a membrane with a porosity of 0.22 µm. Approximately 12 l of filtrate are thus obtained containing N-acetylheparosan.

TABLE I

Composition and Preparation of Medium A and Medium B

Medium A

Dissolve in 900 ml of ultrapurified water in this order:

| | |
|---|---|
| NTA (nitrilotriacetic acid) | 1000 mg |
| $K_2HPO_4$ | 790 mg |
| Glutamic acid | 11,000 mg |
| $MgCl_2.6H_2O$ | 500 mg |
| $K_2SO_4$ | 450 mg |
| $FeSO_4.7H_2O$ | 18 mg |
| $CaCl_2.2H_2O$ | 2 mg |
| NaCl | 500 mg |
| KCl | 5000 mg |
| Solution of trace elements (cf. Table II) | 1 ml |
| Glycerol | 10,000 mg |

Adjust the pH to 7.2 with concentrated potassium hydroxide solution of density 1.38 and make up to 1000 ml with ultrapurified water. Carry out a sterilising filtration through a 0.2 µm membrane.

Glycerol Solution

Dissolve 50 g of glycerol in a sufficient quantity of ultrapurified water and adjust the volume to 1000 ml with the same solvent. Carry out a sterilising filtration through a 0.2 µm membrane.

The antifoaming agent employed during fermentation is Struktol J 673 (Schill and Seilacher ®).

Medium B

The preparation of medium B is identical to that of medium A, apart from the difference that it is advisable additionally to add the buffer (pH 7.2) : 3-morpholinopropanesulphonic acid (M.O.P.S.) after addition of the antifoaming agent.

Table II

Preparation of the Solution of Trace Elements Used in the Preparation of Medium A and Medium B Dissolve (in this order) in 800 ml of ultrapurified water:

| | |
|---|---|
| $H_3BO_3$ | 500 mg |
| $Na_2MoO_4.2H_2O$ | 1930 mg |
| $CoCl_2.6H_2O$ | 11,850 mg |
| $CuSO_4.5H_2O$ | 25 mg |
| $ZnSO_4.7H_2O$ | 2000 mg |
| $AlCl_3.6H_2O$ | 2410 mg |
| Add 100 ml of hydrochloric acid of density 1.19 | |

-continued and make up to 1000 ml with ultrapurified water.

2) Isolation and purification of a N-acetylheparosan largely of high molecular mass Stage a—Ethanolic precipitation Approximately 48 l of 95% (v/v) ethanol are added to the filtrate and the mixture is left to precipitate and settle at 4° C. for 8 h.

The supernatant is removed by pumping and then by centrifuging, and the centrifugation pellet is taken up in approximately 1 l of ultrapurified water.

Stage b—Dialysis

The solution obtained in the above stage is placed in a Nojax 40 bag, composed of a cellulose-based membrane and with a porosity of 24 Å, and is dialysed for 24 h against ultrapurified water (1 volume of solution/6 volumes of water, renewed after 2 h, 8 h and 16 h).

This operation makes it possible to remove the small molecules present in the culture medium, such as salts, sugars, amino acids, oligonucleotides and oligopeptides.

Stage c—Precipitation, dehydration and drying 0.5 M of NaCl and 4 volumes of ethanol are added to 1 volume of the dialysed solution. The precipitate is left to form for 5 min at room temperature. The mixture is centrifuged at 5000 g for 20 min.

The centrifugation pellets are taken up in ethanol, the suspension obtained is stirred and is left standing for 1 h at room temperature. The centrifugation and suspending operations are repeated. The mixture is centrifuged again at 5000 g for 20 min. The centrifugation pellets obtained are dried in an oven under vacuum at 40° C. for 24 h.

Stage d—Grinding to powder

The dry centrifugation pellets are ground using a mortar under anhydrous conditions.

Stage e—Anion exchange chromatography

The ground centrifugation pellet's are taken up in a buffer, called buffer D, composed of 20 mm tris-HCl, pH 7.5, in an amount of 100 ml/g.

The solution obtained is chromatographed on a column for the exchange of strong anions containing an agarose matrix crosslinked with quaternary ammonium groups ("Q-Sepharose fast flow" from Pharmacia®) equilibrated beforehand with buffer D, in an amount of 50 ml of gel per 1 g of powder.

The gel is washed with a sufficient quantity of buffer D to return to the base line of UV detection at 214 mn and then with a 25 mM solution of piperazine whose pH was adjusted to 3.5.

Elution is carried out with a solution of pH 3.5 having the composition: 0.5 M NaCl and 25 mm piperazine. The eluate is neutralised with a 5N NAOH solution.

Stage f—Precipitation, dehydration, drying and grinding

The operations described in Stages c and d above are repeated, without addition of sodium chloride.

The N-acetylheparosan obtained from Stage f is called batch A.

3) Characterisation of the N-acetylheparosan obtained from the various purification stages Nuclear magnetic resonance (NMR) spectrum The proton and $^{13}C$ carbon NMR spectra are compared with those of N-acetylheparosan described by W. F. Vann (Eur. J. Biochem., (1981), 116, 359–364).

Study of the spectra obtained with N-acetylheparosan of batch A confirms the chemical identity of the product with the N-acetylheparosan described by W. F. Vann. It consists of chains of polymers consisting of repeating structures of $\beta$-D-glucuronyl-1,4-$\alpha$-N-acetyl-D-glucosaminyl-(1,4).

Determination of the Molecular Mass Distribution by Steric Exclusion Chromatography First Method The molecular mass distribution is determined by exclusion HPLC under the following conditions:

Column consisting of silica beads having a diameter of 10 $\mu$m and a porosity of 250 Å.

Eluent: 0.5M aqueous sodium sulphate solution.

Flow rate: 1 ml/min.

UV detection at $\lambda=205$ nm.

Calibration is carried out using a range of oligosaccharides derived from heparin, with the following molecular masses: 1324, 1883, 2436, 3411, 3996, 4535, 4995, 5365, 6150, 6671, 7542, 8655, 10,088, 11,561, 12,950, 14,809, 17,387 and 22,674 D.

In view of this range of calibrations, only the molecular masses between 930 D and 57,000 D are precisely evaluated. It is assumed that the optical density detected is proportional to the quantity of N-acetylheparosan. The precision of the method diminishes significantly for high molecular masses and especially for those above $5\times10^6$ D.

The elution profile of the exclusion chromatography of batch A makes it possible to conclude that the distribution is polydisperse and that it contains a majority peak at approximately $2\times10^6$ D. A fraction by weight at least equal to 70% of batch A has a mass of between $1.0\times10^5$ and $3.0\times10^5$ D.

Second Method

The results were verified by exclusion HPLC using a light-scattering detector.

Columns: System composed of one precolumn and three successive columns:
- PL-Aquagel—OH ® (precolumn)
- PL-Aquagel—OH ® 40 ®
- PL-Aquagel—OH ® 50 ®
- PL-Aquagel—OH ® 60 ®

Eluent: 400 ppm aqueous $NaN_3$ solution

Flowrate: 1 ml/min

Room temperature

Detection: differential refractometer/light scattering coupling. The response of the mass detector (light scattering) is proportional to:

$$C \times (dn/dc)^2 \times M_w$$

C = concentration
dn/dc = refractive index increment
Mw = mean molecular mass

The calculation of the dn/dc ratio was carried out from the responses of the differential refractometer by taking into account those of two reference samples (Dextran, Mw=70,000 D and 150,000 D).

This method has confirmed that a fraction by weight at least equal to 70% of batch A has a mass of between $1.0\times10^5$ and $3.0\times10^5$ D and that the elution profile obtained after exclusion chromatography of batch A contains a majority peak at approximately 210,000 D.

Monitoring of the Molecular Mass Distribution by Electrophoresis on Polyacrylamide Gel These samples to be analysed, as well as an end-of-migration marker comprising bromophenol blue, were subjected to electrophoresis in Tris-borate buffer in a 15% polyacrylamide gel obtained by polymerisation of a 29/1 mixture of acrylamide and N,N'-methylene-bisacrylamide.

The migration is carried out under 40 mA for approximately 4 h on a gel 18 cm long until the end-ofmigration marker exits. The gel is then coloured with alcian blue and then with silver according to the technique of S. Pelkonen et al. (J. Bact., (1983), 170, 6, 2646) which is specific for acidic polysaccharides.

This analysis by electrophoresis was carried out on the partially purified product obtained from Stage a and on the purified product resulting from the final stage for the purpose of verifying the absence of significant changes in the molecular mass distribution of the N-acetylheparosan during purification.

Observation of the profiles obtained for the partially purified product obtained from Stage a and for the product purified in the final stage reveals no significant differences (presence of bands of comparable intensity at the same migration distances). Thus, there is no significant change in the molecular mass distribution of the N-acetylheparosan during its purification.

Quantitative Determination of the Uronic Acids

The quantity of uronic acid per mass unit of the purified product obtained from the final stage was determined by colorimetry according to the method described by T. Bitter, (Analytical Biochemistry, (1962), 4, 330–334). This method of quantitative determination is based on the reaction of glycosaminoglycans with carbazole in hot acidic medium, which causes a pink coloration proportional to the quantity of uronic acid released. In this specific case, the acid is glucuronic acid.

For batch A, the partially purified product obtained from the final stage has a uronic acid level of 2.2 $\mu$mol/mg.

Spectrophotometry in the Ultraviolet and Visible Region

The purified product (batch A) is dissolved in ultrapurified water and the solution obtained (C=1 mg/ml) is placed in a vessel with an optical path of 1 cm. Its absorption spectrum is recorded between 200 and 600 nm.

The spectrum obtained makes it possible to confirm, in particular on the basis of the absorption at 256 nm, that batch A contains less than 1% of ADN.

Quantitative Determination of the Total Proteins

The protein assay kit marketed by Biorade ® is used for determining the total proteins. The determination method is based on the fact that the wavelength for maximum absorbance of an acidic solution of Coomassie Brilliant Blue g-250 moves from 465 nm to 595 nm when proteins come to be bound thereto (Reisner et al., Anal Biochem, (1975), 64, 509).

The level of total proteins in batch A is less than 1.5%.

Quantitative Determination of the Free Amino Groups (NH$_2$)

This quantitative determination was carried out according to the method described by Zensaku Yosizawa et al., in Biochemica et Biophysica Acta, (1967), 141, 358–365.

The NH$_2$ level parameter (expressed in $\mu$mol/mg) is an indicator of quantities of deacetylated $\beta$-D-glucuronyl-1,4-$\alpha$-N-acetyl-D-glucosaminyl-(1,4) units and of possible impurities present which contain a free amino group.

Batch A has a NH$_2$ level of 0.1 $\mu$mol/mg.

PREPARATION II

Preparation of a Largely High Molecular Mass N-acetylheparosan (Process II)

1) Culturing of the bacterial strain *Escherichia coli* (K5) and separation of a filtrate containing N-acetylheparosan The culturing of the strain *Escherichia coli* SEBR 3282 and the separation of a filtrate containing N-acetylheparosan were carried out according to the method described in Preparation I.

2) Isolation and purification of a largely high molecular mass N-acetylheparosan Stage a—Dialysis 375 ml of filtrate are subjected to a dialysis according to the process described in Preparation I, [2] Isolation and purification of a largely high molecular mass N-acetylheparosan, Stage b]. After dialysis, approximately 1020 ml of purified solution are obtained.

Stage b—Purification in acidic medium

A sufficient quantity of a 5N HCl solution to obtain a pH of 3.5 is added to the dialysed solution. The precipitate formed is removed by centrifuging and the solution is then acidified with the same acid (5N HCl) to obtain a pH of 1.8. A precipitate may be formed which will be removed by centrifuging.

The solution is then neutralised using a 5N NAOH solution.

Stage c—Precipitation, dehydration and drying

A sufficient quantity of sodium chloride is added to the neutralised solution to obtain a 0.5M NaCl solution and then 4 volumes of ethanol are added. The precipitate is allowed to form for 5 min at room temperature. The mixture is centrifuged at 5000 g for 20 min.

The centrifugation pellets are taken up in ethanol, the suspension obtained is stirred and is left standing for 1 h at room temperature. The centrifuging and suspending operations are repeated. The mixture is centrifuged again at 5000 g for 20 min.

The centrifugation pellets obtained are dried in an oven under vacuum at 40° C. for 24 h.

Stage d—Alkaline hydrolysis and dialysis

The product obtained in the above stage after drying is dissolved at 2.5% (w/v) in a 0.25N NAOH solution. The solution thus obtained is maintained for 2 hours at 50° C.

The solution is then neutralised with a 5N HCl solution and the solution containing the polysaccharide is then subjected to a dialysis according to the process described in Preparation I, [2] Isolation and purification of a largely high molecular mass N-acetylheparosan, Stage b].

After dialysis, approximately 990 ml of solution are obtained.

Stage e—Anion exchange chromatography

Sufficient quantities of piperazine, EDTA and triton X-100 (Prolabo ®) are added to the dialysed solution to obtain concentrations respectively of 25 mM for piperazine, 2 mM for EDTA and 0.2% (v/v) for triton X-100.

The pH is then adjusted to 3.5 with a 5N HCl solution. This solution is placed on a 400 ml Q-Sepharose Fast Flow column, equilibrated in a piperazine buffer containing 25 mM of piperazine, 2 mM of EDTA and 0.2 mM of triton X-100 (pH=3.5).

The column is washed with the piperazine buffer, eluted with a 0.5M NaCl solution and the product is then precipitated with 4 volumes of ethanol.

The product is dried under vacuum at 40° C. Approximately 9.85 g of N-acetylheparosan are thus obtained.

Stage f—Steric exclusion chromatography 4 g of the product obtained in the above stage are dissolved in 60 ml of a buffer solution, which has the composition: 20 mM tris-HCl, pH 7.5, and 1 M NaCl, and are then passed through a 200 ml octyl Sepharose ® column equilibrated beforehand with the same buffer.

4 volumes of ethanol are added to the nonretained fraction. The precipitate formed is washed and then dried at 40° C. under vacuum.

3.90 g of N-acetylheparosan (batch B) are thus obtained.

3) Characterisation of the N-acetylheparosan obtained from the various purification stages Nuclear magnetic resonance (NMR) spectrum Study of the proton and $^{13}C$ carbon NMR spectra obtained with this N-acetylheparosan confirms the chemical identity of the product with the N-acetylheparosan described by W. F. Vann (Eur. J. Biochem. (1981) 116, 359–364).

Determination of the molecular mass distribution by steric exclusion chromatography The molecular mass distribution is determined by steric exclusion HPLC according to the methods used for the determination of the molecular mass distribution of N-acetylheparosans described in Preparation I. A fraction by weight at least equal to 60% of the chains which constitute batch B resulting from Preparation II has a molecular mass of between $5.0 \times 10^4$ and $2.5 \times 10^5$ D.

Quantitative determination of the uronic acids

The N-acetylheparosan resulting from Stage e has a uronic acid level of 2.2 μmol/mg.

Spectrophotometry in the ultraviolet and visible region

The spectrum obtained makes it possible to affirm that the N-acetylheparosan obtained contains less than 1% DNA.

Quantitative determination of the total proteins

The total proteins level in batch B is less than 1%.

Quantitative determination of the free amino groups ($NH_2$)

The $NH_2$ level is less than 0.1 μmol/mg.

PREPARATION II

Preparation of a Largely High Molecular Mass N-acetyl-heparosan (Process III)

1) Culturing of the bacterial strain *Escherichia coli* (K5)

Culturing of the strain *Escherichia coli* SEBR 3282 was carried out according to take method described in Preparation I. Approximately 12 l of culture containing N-acetylheparosan are obtained.

2) Preliminary purification

Stage a—Centrifuging

At the end of culturing, the suspension obtained is centrifuged at 8000 rev/min (or between 11,000 and 14,000 g) for 20 min.

Stage b—Bringing into contact with an alkaline solution

After centrifuging, the pellet is removed and the supernatant is brought into contact with a 0.1N NAOH solution for approximately 1 hour.

Stage c—Prefiltration

The solution obtained in the above stage is subjected to a prefiltration through a polypropylene 3M ® series 300 filter.

Stage d—Concentration through a membrane with a predetermined threshold cutoff value.

The filtrate obtained in Stage c is concentrated through a cartridge containing Amicon ® hollow fibres with a threshold cutoff value of 30,000 D or equivalent. A solution is thus obtained which is concentrated in high molecular mass N-acetylheparosan.

Stage e—Dialysis

The solution which is concentrated in high molecular mass N-acetylheparosan is dialysed against ultrapurified water, still on the Amicon ® system, at a very high dilution factor ($>10,000$).

3) Isolation and purification of a largely high molecular mass N-acetylheparosan The isolation and purification are carried out as shown in Preparation I [2) Isolation and purification of a largely high molecular mass N-acetylheparosan, Stage c-Stage f] and a N-acetylheparosan (batch C) is obtained which has characteristics similar to those of batch A, or as shown in Preparation II [2) Isolation and purification of a largely high molecular mass N-acetylheparosan, Stage a–Stage f].

PREPARATION IV

Preparation of a Largely High Molecular Mass N-acetyl-heparosan (Process IV)

1) Culturing of the bacterial strain *Escherichia coli* (K5)

Culturing of the strain *Escherichia coli* SEBR 3282 was carried out according to the method described in Preparation I by using, as culture medium, medium C in place of medium A and medium D in place of medium B.

The composition of medium C and medium D is specified in Table III (cf. following page).

Approximately 12 l of filtrate containing N-acetylheparosan are thus obtained.

2) Isolation and purification of a largely high molecular mass N-acetylheparosan The isolation and purification are carried out as described in Preparation I, [2) Isolation and purification of a largely high molecular mass N-acetylheparosan, Stage a, Stage f]. Batch D is thus obtained.

3) Characterisation of the N-acetylheparosan obtained

Determination of the molecular mass distribution by exclusion chromatography

The methods used are identical to those described in Preparation I [3) Characterisation of the N-acetylheparosan obtained from the various purification stages: Determination of the molecular mass distribution by steric exclusion chromatography—First and second method].

Examination of the elution profile of the steric exclusion chromatography of batch D makes it possible to conclude that the molecular mass distribution is polydisperse and that it contains a majority peak at approximately 110,000 D.

A fraction by weight at least equal to 75% of batch D has a mass of between $1.0 \times 10^4$ and $2.5 \times 10^5$ D.

Quantitative determination of the uronic acids

The uronic acid level is 2.0 μmol/mg.

Quantitative determination of the free amino groups ($NH_2$)

The $NH_2$ level in the batch is less than 0.1 μmol/mg.

TABLE III

Composition and Preparation of Medium C and Medium D

Medium C

Medium C is prepared by combining the three sterile solutions below:

Solution No. 1

Dissolve in 700 ml of ultrapurified water in this order:

| | |
|---|---|
| Complexing agent: N-[tris(hydroxymethyl)methyl]-glycine (Tricine marketed by Fluka ®) | 360 mg |
| $FeSO_4.7H_2O$ | 280 mg |
| $CaCl_2.2H_2O$ | 6.7 mg |
| $MgCl_2.6H_2O$ | 1270 mg |
| $K_2SO_4$ | 500 mg |
| KCl | 5000 mg |
| Casein hydrolysate (main source of amino acids HY CASE SF (marketed by Sheffield ®) | 25,000 mg |
| Yeast extract (marketed by Difco ®) | 18,000 mg |
| Solution of trace elements (cf. Table II, Preparation I) | 1 ml |

Antifoaming agent Struktol J673 (marketed by Schill and Seilachek ®): a few drops from a Pasteur pipette.

Adjust the PH to 7.4 with a KOH solution (d=1.38) and make up to 850 ml with ultrapurified water. Autoclave the medium for 45 min at 120° C.

Solution No. 2

Dissolve 5 g of $K_2HPO_4$ in approximately 40 ml of ultrapurified water and then adjust to 50 ml with the same solvent. Filter the solution obtained through a filter with a porosity of 0.2 μm.

Solution No. 3

Dissolve 20.7 g of glycerol in a sufficient quantity of ultrapurified water and adjust the volume to 100 ml with the same solvent. Autoclave at 110° C. for 30 minutes.

Medium D

The preparation of medium D is identical to that of medium C, apart from the difference that it is advisable additionally to add 20 g of buffer (pH=7.2): 3-morpholinopropanesulphonic acid after addition of the antifoaming agent.

PREPARATION V

Preparation of a Heparosan (40% N-deacetylated Derivative)

3.7 g of the N-acetylheparosan described in Preparation IV (batch D) are dissolved in 74 ml of 1N NaOH. The solution is brought to 50° C. and is left to react at this temperature for 8 hours with stirring and under nitrogen. The pH is then adjusted to approximately 8 with a 2N HCl solution, the solution obtained is dialysed against ultrapurified water and is then lyophilised.

After lyophilising, 2.91 g of product (batch E) are obtained.

Degree of N-deacetylation

Quantitative determination of the free amino groups ($NH_2$) of the product obtained after lyophilisation shows that the N-acetylheparosan was 40% N-deacetylated.

PREPARATION VI

Preparation of a N-sulphated Heyarosan (80% N-deacetylated Derivative)

A N-acetylheparosan, called batch F, prepared according to the process described in Preparation II is used as starting material for the various chemical modifications.

The uronic acid level in this product is 2.41 μmol/mg.

Stage a—Partial N-deacetylation 1.9 g of batch F are dissolved in 38.5 ml of 2N NaOH. The solution is brought to 50° C. and is left to react at this temperature for 8 hours under nitrogen.

The pH is then adjusted to 8.25 with addition of 2N HCl. The solution is dialysed against ultrapurified water and is then lyophilised.

1.6 g of product are thus obtained.

Degree of N-deacetylation

Quantitative determination of the free amino groups ($NH_2$) shows that the N-acetylheparosan was 80% N-deacetylated.

Stage b—N-Sulphation 1.33 g of product obtained in the above stage are dissolved in 57 ml of ultrapurified water, 1.9 g of $Na_2CO_3$ and 1.9 g of sulphur trioxide/trimethylamine complex are added and the mixture is brought to 55° C. for 20 hours. The conductivity of the solution is then adjusted to that of a 0.5M NaCl solution with addition of demineralised water and the solid is precipitated with 4 volumes of ethanol. The solid is centrifuged, the pellet is taken up in a 0.5M NaCl solution, and the solid is precipitated with 4 volumes of ethanol and centrifuged.

The pellet is dissolved in ultrapurified water and the solution is dialysed against ultrapurified water according to the process described in Preparation I and then lyophilised.

1.809 g of N-sulphated heparosan (batch F1) is thus obtained.

PREPARATION VII

Preparation of a Low Molecular Mass N-sulphated Heyarosan (80% N-deacetylated Derivative) by Depolymerisation With Nitrous Acid: (Final Nitrite Concentration: 0.04 M)

Stage a—Cleavage with sodium nitrite 1 g of the product obtained in Preparation VI is dissolved in 8 ml of ultrapurified water. The pH of the solution is adjusted to 2.5 with 2N HCl. 0.276 ml of a 100 mg/ml aqueous sodium nitrite solution is added to the vigorously stirred solution at room temperature under a flow of nitrogen (final nitrite molarity: 0.04 M). The pH is immediately readjusted to 2.5 with 2N HCl and the total volume of the solution is made up to 10 ml. Stirring is maintained for 2 hours under a flow of nitrogen.

Stage b—Reduction of the 2,5-anhydromannose groups formed

The pH of the solution is adjusted to 7.0 with 2N sodium hydroxide solution, 0.2 g of sodium borohydride is then added and the mixture is stirred for 15 hours at room temperature while exposed to the air.

The excess borohydride is hydrolysed by acidifying to pH 3.5 with 10% acetic acid. The reaction solution is stirred for 15 minutes and the pH is then adjusted to 7.0 with 2N sodium hydroxide solution.

The reaction product is precipitated with 4 volumes of ethanol, centrifuged, washed with pure ethanol and dried under vacuum at 60° C.

980 mg of low molecular mass, depolymerised N-sulphated heparosan (80% N-deacetylated derivatives) are thus obtained having, at the reducing end, a 2,5-anhydromannitol group (batch G).

Determination of the molecular mass distribution by steric exclusion HPLC

The molecular mass distribution is determined by steric exclusion HPLC under the following conditions: TSK 2000 (Toyo Soda) column.

Mobile phase: 0.5 M aqueous sodium sulphate solution

Flow rate: 1 ml/min

UV detector at $\lambda = 205$ nm

Calibration is carried out using a range of oligosaccharides derived from heparin as described in Preparation I [3] Characterisation of the N-acetylheparosan obtained from the various purification stages: Determination of the molecular mass distribution by steric exclusion chromatography—First method].

Certain results deduced from the elution profile are collated in Table IV below.

$MW_1$ represents the molecular mass such that a 1% fraction, by weight, of the product has a molecular mass higher than $MW_1$.

$MW_2$ represents the molecular mass such that a 10% fraction, by weight, of the product has a molecular mass higher than $MW_2$.

$MW_4$ represents the molecular mass such that a 10% fraction, by weight, of the product has a molecular mass lower than $MW_4$.

$MW_5$ represents the molecular mass such that a 1% fraction, by weight, of the product has a molecular mass lower than $MW_5$.

$MW_3$ represents the molecular mass corresponding to the absorption maximum.

Table IV

TABLE IV

| Molecular mass distribution of the product obtained in Preparation VII (Batch G) | | | | |
|---|---|---|---|---|
| $MW_1$ | $MW_2$ | $MW_3$ | $MW_4$ | $MW_5$ |
| 16,939 | 8843 | 3716 | 1757 | 925 |

PREPARATION VIIII

Preparation of a Low Molecular Mass N-sulphated Heparosan (80% N-deacetylated Derivative) by Depolymerisation with Nitrous Acid: (Final Nitrite Concentration: 0.03 M)

The preparation is carried out as described in Preparation VII by adding 0.208 ml of a 100 mg/ml sodium nitrite solution instead of 0.276 ml.

990 mg of product (batch H) are thus obtained.

The molecular mass distribution is determined by steric exclusion HPLC as described in Preparation VII.

Certain results deduced from the elution profiles are collated in Table V.

$MW_1$, $MW_2$, $MW_3$, $MW_4$ and $MW_5$ have the meanings given for Table IV.

TABLE V

| Molecular mass distribution of the product obtained in Preparation VIII (Batch H) | | | | |
|---|---|---|---|---|
| $MW_1$ | $MW_2$ | $MW_3$ | $MW_4$ | $MW_5$ |
| 19,856 | 11,146 | 5377 | 2460 | 1536 |

N,O-SULPHATED HEPAROSANS

Example 1

N,O-Sulphated heparosans: 80% N-deacelylated derivatives having a deggee of sulphation of 2.6

Stage a—Formation of the tetrabutylammonium salt 800 mg of N-sulphated heparosan obtained according to Preparation VI (the N-acetylheparosan used as starting material being prepared according to Preparation IV) are dissolved in 100 ml of water. This solution is placed on an ion exchange column based on polystyrene crosslinked with divinylbenzene (Dow Chemical ® Dowex 50 W 8 20-50 Mesh), conditioned beforehand in acidic medium, so as to regenerate the acidic form of the product. The pH of the eluate is brought to 7 with a solution of tetrabutylammonium hydroxide (40% w/v). Addition of the solution is stopped when the eluate is completely neutralised (pH=7). The solution is lyophilised.

Approximately 1.3 g of salt are obtained after lyophilisation.

Stage b—O-Sulphation

The salt obtained in the above stage is dissolved in 80 ml of formamide and 5.6 g of sulphur trioxide/ pyridine complex (marketed by Aldrich ® under reference S755-6) are added. The mixture is left to react for 6 hours at 30° C. and then 16 ml of 2M NaCl are added. The pH is brought to 7 with a 5N NAOH solution and precipitation is effected with 2 volumes of ethanol. The precipitate is taken up in a 0.5M NaCl solution, reprecipitation is effected with 2 volumes of ethanol, dialysis is carried out against ultrapurified water and concentration is carried out on a Rotavapor.

Stage c—Gel filtration

The concentrated solution obtained in stage b is fractionated by gel filtration using a Sephacryl S 300 HR column and using a 0.5M NaCl solution as eluent.

The fractions are collected containing an N,O-sulphated heparosan consisting of chains having mean molecular masses of from 100,000 to 200,000 D, as well as the fractions containing an N,O-sulphated heparosan consisting of chains having mean molecular masses of approximately 50,000 D and approximately 12,000 D.

5 volumes of ethanol are added to each of these three fractions, they are subjected to dialysis against ultrapurified water and the solutions obtained after dialysis are subjected to lyophilisation.

3 batches of N,O-sulphated heparosan are thus obtained:

batch 1A is an N,O-sulphated heparosan consisting of chains having a mean molecular mass of 150,000 to 200,000 D. This N,O-sulphated heparosan consists of at least 70% by mass of chains having a molecular mass of between $1.0 \times 10^5$ and $5.0 \times 10^5$ D. 0.140 g of this N,O-sulphated heparosan is isolated.

batch 1B is an N,O-sulphated heparosan consisting of chains having a mean molecular mass of approximately 50,000 D. This N,O-sulphated heparosan consists of at least 70% by mass of chains having a molecular mass of between $2.0 \times 10^4$ and $1.0 \times 10^5$ D. 0.350 g of this N,O-sulphated heparosan is isolated.

batch 1C is an N,O-sulphated heparosan consisting of chains having a mean molecular mass of 12,000 D. Approximately 0.100 g of this last product is isolated.

The characteristics of the three batches of N,O-sulphated heparosan described in this example are collated in Table VI.

TABLE VI

Characteristics of N,O-sulphated heparosans corresponding to batches 1A, 1B and 1C

| | Uronic acid level ($\mu$mol/mg) | $NH_2$ Level ($\mu$mol/mg) | Degree of deacetylation | Degree of sulphation (sulphate/carboxyl ratio) |
|---|---|---|---|---|
| Batch 1A | 1.48 | <0.01 | 80% | 2.6 |
| Batch 1B | 1.45 | <0.01 | 80% | 2.6 |
| Batch 1C | 1.45 | <0.01 | 80% | 2.6 |

The degree of sulphation, also called the sulphate/carboxyl ratio, is the mean number of sulphate groups, contained in a disaccharide structure, per carboxyl group contained in this same structure; it is measured by the conductimetric method for quantity determination of the sulphate group and of the carboxyl group, described by B. Casu et al., in Carbohydrate Research, (1975), 39, 168–176.

Example 2

N,O-Sulphated heparosans: 40% N-deacetylated derivatives having a degree of sulphation of 2.1

Stage a—Formation of the tetrabutylammonium salt

A heparosan, prepared according to Preparation V (batch E), is used as starting material and the salt is prepared according to the method described in Example 1, Stage a. The N-acetylheparosan used as starting material for the heparosan preparation was prepared according to the process of Preparation I.

Stage b—Partial N,O-sulphation 421 mg of the salt obtained in the above stage are dissolved in 35 ml of dimethylformamide and 3.71 g of the sulphur trioxide/pyridine complex are added. The mixture is left to react with stirring for 6 h at room temperature. Sodium chloride is added to one volume of the reaction mixture until a solution is obtained which has a sodium chloride concentration of 0.33 M and then 2 volumes of ethanol are added. The precipitate is left to form. The mixture is centrifuged and the supernatant is discarded. The centrifugation pellet is taken up in a 0.5M NaCl solution which is neutralised. 2 volumes of ethanol are then added. The precipitate is left to form, the mixture is centrifuged and the centrifugation pellet is taken up in ultrapurified water.

The solution is dialysed against ultrapurified water and lyophilised.

The lyophilisate obtained has the following characteristics:

free $NH_2$ level: 0.10 $\mu$mol/mg
degree of sulphation: 1.9 per disaccharide unit Stage c—Complete N-sulphation 1 part by weight of N,O-sulphated product, 1 part by weight of sodium bicarbonate, and 1 part by weight of the sulphur trioxide/trimethylamine complex are mixed in a volume of 20 ml of ultrapurified water per gram of N,O-sulphated product introduced and the mixture is left to react at 55° C. with stirring for 20 h. The reaction mixture is then diluted (dilution factor 10) and then the conductivity of the solution obtained is adjusted to that of a 0.5M sodium chloride solution.

Precipitation is next carried out by addition of 2 volumes of ethanol, then centrifuging after which the centrifugation pellets are taken up in a 0.5M NaCl solution, and then a second precipitation is carried out by addition of 2 volumes of ethanol. After being taken up in ultrapurified water and dialysed against ultrapurified water, the product is lyophilised and dried at 40° C. under vacuum.

The lyophilisate obtained (batch 2) has the following characteristics:

free $NH_2$ level: 0.02 $\mu$mol/mg
degree of sulphation: 2.1 per disaccharide unit It is observed that the residual $NH_2$ level (0.02 $\mu$mol/mg) is low and less than that of the N,O-sulphated heparosan obtained from the partial N,O-sulphation stage. This shows the complete nature of the N-sulphation reaction.

Batch 2 contains at least 70% by mass of chains having a molecular mass of between $2.0 \times 10^4$ D and $2.5 \times 10^5$ D.

Example 3

N,O-Sulphated heparosan: 80% deacetylated derivative having a degree of sulphation of 2.6

3.35 g of an N-sulphated heparosan, prepared according to the process described in Preparation VI (Stages a and b), are used as starting material.

This compound was obtained from 4 g of an N-acetylheparosan prepared according to the process described in Preparation III.

70% of the N-sulphated heparosan used as starting material consists of chains having a molecular mass of between 20,000 and 150,000 D, and it has the following characteristics:

Uronic acid level: 1.5 $\mu$mol/mg
Free $NH_2$ level: 0.10 $\mu$mol/mg
Degree of deacetylation: 80%

Stage a—Formation of the tetrabutylammonium salt

The N-sulphated heparosan is dissolved in 400 ml of ultrapurified water and the salt is prepared as described in Example 1 (Stage a).

After lyophilising, 6.66 g of salt are obtained.

Stage b—O-Sulphation 297 mg of the salt obtained in the above stage are dissolved in 20 ml of formamide and 1 g of the sulphur trioxide/pyridine complex is added, and then the preparation is as described in Example 1 (Stage b).

260 mg of a N,O-sulphated heparosan are thus obtained.

The characteristics of this N,O-sulphated heparosan (batch 3) are shown in Table VII.

TABLE VII

Characteristics of the product corresponding to Batch 3

| | Uronic acid level ($\mu$mol/mg) | $NH_2$ Level ($\mu$mol/mg) | Degree of deacetylation | Degree of sulphation (sulphate/carboxyl ratio) |
|---|---|---|---|---|
| Batch 3 | 1.50 | <0.02 | 80% | 2.60 |

The molecular mass distribution of the chains which constitute the N,O-sulphated heparosan of batch 3 is determined by steric exclusion chromatography according to the technique described in Preparation I (First method).

The molecular mass corresponding to the absorption maximum was estimated at 80,000-150,000 D. Batch 3 contains at least 70% by mass of chains having a molecular mass of between $2.5 \times 10^4$ D and $2.5 \times 10^5$ D, and at least 60% by mass of chains having a molecular mass of between $4.5 \times 10^4$ and $2.5 \times 10^5$ D.

USE OF HIGH MOLECULAR MASS N-SULPHATED HEPAROSANS AND N,O-SULPHATED HEPAROSANS FOR THE PREPARATION OF LOW MOLECULAR MASS N,O-SULPHATED HEPAROSANS

Example 4

Preparation of a Low Molecular Mass N,O-sulphated Heparosan from a High Molecular Mass N,O-sulphated Heparosan: 80% Deacetylated Derivative having a Degree of Sulphation of 2.5

Stage a—Formation of the tetrabutylamonium salt

The preparation is carried out as described in Example 1, stage a, using 5 g of N-sulphated heparosan obtained according to Preparation VI and sufficient quantities of solvents and reactants.

After lyophilising, approximately 9.3 g of salt are obtained.

Stage b—O-Sulphation 8.10 g of the previously obtained tetrabutylanunonium salt are dissolved in 450 ml of anhydrous formamide. The solution is passed through a 290 ml column containing a 4 Å molecular sieve. 27 g of a sulphur trioxide/pyridine complex are then added thereto and the mixture is incubated for 6 hours at 30° C.

A sufficient quantity of 2M NaCl solution is then added so that the reaction mixture has a final sodium chloride concentration of 0.5M. The mixture is then neutralised with 1N NAOH and is precipitated with 2 volumes of ethanol.

The precipitate is taken up with a 0.5M NaCl solution and is reprecipitated with 2 volumes of ethanol. After centrifuging, the pellet is taken up in a minimum volume of water and dialysed for 15 hours. The solution obtained after dialysis is then subjected to lyophilisation.

5.8 g of product are thus obtained.

Stage c—Depolymerisation with nitrous acid (final nitrite concentration: 0.035M)

2 g of product obtained in stage b are dissolved in 17 ml of ultrapurified water at 22° C. The solution is degassed by placing under vacuum for one hour. It is then vigorously stirred under a flow of nitrogen, the pH is lowered to 2.5 with 5N HCl and 0.484 ml of 100 mg/ml sodium nitrite is added.

The pH is immediately readjusted to 2.5 and the volume is made up to 90 ml with ultrapure water (final sodium nitrite concentration in the reaction solution equal to 0.035M).

Stirring is maintained for 3 hours at room temperature under a stream of nitrogen. The pH is then brought to 7.0 using 5N sodium hydroxide solution and 0.4 g of sodium borohydride are added. The solution is stirred for 15 hours while exposed to the air. The excess sodium borohydride is then destroyed by acidifying with 30% acetic acid to a pH of 3.5. The reaction solution is then subjected to vigorous stirring for 15 minutes while exposed to the air and the pH is adjusted to 7 with addition of 5N sodium hydroxide solution.

The fragmented heparosan is recovered by precipitating with 4 volumes of ethanol, centrifuging, washing with ethanol on a sintered Büchner funnel and drying under vacuum at 60° C.

8.7 g of product are thus obtained.

Stage d—Gel filtration 1.6 g of product obtained in stage c are dissolved in 15 ml of 0.5M NaCl and gel-filtered on a 5 cm $\times$ 100 cm Sephacryl S 200 HR (Pharmacia) column equilibrated beforehand with 0.5M NaCl (flow rate of 8 ml/min). The eluate is collected in 30 40-ml fractions. The molecular mass of the N,O-sulphated heparosan cleavage products from each of the fractions is assessed by steric exclusion HPLC on a TSK 2000 column according to the method described in Preparation VII.

The fractions having a mean molecular mass of between approximately 5500 and 8000 D are combined.

The product contained in these fractions is recovered by precipitating with 4 volumes of ethanol, centrifuging, dialysing and lyophilising.

The characteristics of this low molecular mass N,O-sulphated heparosan (Batch 4) are shown in Table VIII.

TABLE VIII

| Characteristics of the product corresponding to Batch 4 | | | |
|---|---|---|---|
| Uronic acid level (µmol/mg) | NH$_2$ level (µmol/mg) | Degree of deacetylation | Degree of sulphation (sulphate/carboxyl ratio) |
| Batch 4 | 1.40 | <0.02 | 80% | 2.50 |

The molecular mass distribution of the chains which constitute the low molecular mass N,O-sulphated heparosan (Batch 4) is shown in Table IX. It was assessed by steric exclusion HPLC as described in Preparation VII.

$MW_1$, $MW_2$, $MW_3$, $MW_4$ and $MW_5$ have the meanings given for Table IV.

TABLE IX

| Molecular mass distribution of the product corresponding to Batch 4 | | | | |
|---|---|---|---|---|
| $MW_1$ | $MW_2$ | $MW_3$ | $MW_4$ | $MW_5$ |
| 14,887 | 9445 | 6912 | 5067 | 2754 |

Example 5

Preparation of a Low Molecular Mass N,O-sulphated Heparosan from a High Molecular Mass N,O-sulphated Heparosan: 80% Deacetylated Derivative having a Degree of Sulphation of 2.9

Stage a—Depolymerisation of an N-sulphated heparosan, 80% N-deacetylated derivative, with nitrous acid (final nitrite concentration: 0.035M)

9 g of an N-sulphated heparosan identical to Preparation VI are dissolved in 85 ml of ultrapurified water at 22° C. The solution is degassed by placing under vacuum for one hour. It is then stirred vigorously under a flow of nitrogen, the pH is lowered to 2.5 using 5N HCl and 2.17 ml of 100 mg/ml sodium nitrite are added. The pH is immediately readjusted to 2.5 and the volume is made up to 90 ml with ultrapure water (final sodium nitrite concentration in the reaction mixture equal to 0.035M).

Stirring is maintained for 3 hours at room temperature under a stream of nitrogen. The pH is then brought to 7.0 using 5N NAOH and 1.8 g of sodium borohydride are added. The solution is stirred for 15 hours while exposed to the air. The excess borohydride is then destroyed by acidifying with 30% acetic acid to a pH of 3.5. The reaction solution is then subjected to vigorous stirring for 15 minutes while exposed to the air. The pH is adjusted to 7.0 with addition of 5N NAOH.

The fragmented N-sulphated heparosan is recovered by precipitating with 4 volumes of ethane, centrifuging, washing with ethanol on a sintered Büchner funnel and drying under vacuum at 60° C.

8.7 g of product are finally obtained.

The molecular mass distribution of the chains which constitute the low molecular mass (Batch 5A) N-sulphated heparosan (80% N-deacetylated derivative) obtained, was assessed by steric exclusion HPLC as described in Preparation VII.

The results deduced from the chromatographic profile are shown in Table X. $MW_1$, $MW_2$, $MW_3$, $MW_4$ and $MW_5$ have the meanings given for Table IV.

TABLE X

| Molecular mass distribution of the product corresponding to Batch 5A | | | | |
|---|---|---|---|---|
| $MW_1$ | $MW_2$ | $MW_3$ | $MW_4$ | $MW_5$ |
| 14,282 | 8999 | 3805 | 2177 | 1536 |

All the chains which constitute the N-sulphated heparosan of Batch 5A contain, at the reducing end, a structure of formula (c) in which G represents a hydrogen atom.

Stage b—Gel filtration 1.6 g of product obtained in the above stage are dissolved in 15 ml of 0.5M NaCl and gel-filtered on a 5 cm × 100 cm Sephacryl S 200 HR (Pharmacia) column, equilibrated beforehand with 0.5M NaCl, with a flow rate of 8 ml/min. The eluate is collected in 30×40 ml fractions. The molecular mass of the heparosan cleavage products from each of the fractions is assessed by steric exclusion HPLC on a TSK 2000 column according to the method described in Preparation VII.

The fractions having a mean molecular mass of between approximately 5000 and 7000 D (Batch 5B1), on the one hand, and between 3500 and 5000 D (Batch 5B2), on the other hand, are combined.

The fragmented N-sulphated heparosan contained in Batches 5B1 and 5B2 is recovered by precipitating with 4 volumes of ethanol, centrifuging, dialysing and lyophilising.

0.5 g corresponding to Batch 5B1 and 0.45 g corresponding to Batch 5B2 are finally obtained.

The molecular distribution of these two heparosans is analysed by steric exclusion HPLC, as described in Preparation VII, and the results are given in Table XI.

$MW_1$, $MW_2$, $MW_3$, $MW_4$ and $MW_5$ have the meanings given for Table IV.

TABLE XI

| Molecular mass distribution of the products corresponding to Batches 5B1 and 5B2 | | | | | |
|---|---|---|---|---|---|
| | $MW_1$ | $MW_2$ | $MW_3$ | $MW_4$ | $MW_5$ |
| Batch 5B1 | 9943 | 8051 | 6357 | 4611 | 2460 |
| Batch 5B2 | 7800 | 6236 | 4088 | 2400 | 1536 |

Stage c—O-Sulphation of the low molecular mass N-sulphated, N-deacetylated heparosan cleavage products 840 mg of Batch 5B1 are converted to tetrabutylammonium salt by passing through Dowex resin, acidified beforehand, and neutralising with tetrabutylammonium hydroxide.

The tetrabutylammonium salt is recovered and lyophilised.

Process I: Sulphation by the sulphur trioxide/pyridine complex 420 mg of the N-sulphated, N-deacetylated heparosan in the form of the tetrabutylammonium salt obtained above are dissolved in 42 ml of anhydrous formamide (the mass shown corresponds to N-sulphated, N-deacetylated heparosan in the nonsalified form). The solution is passed through a 15 ml column containing a 4 Å molecular sieve. 1.4 g of a sulphur trioxide/pyridine complex are then added thereto and the mixture is incubated for 6 hours at 30° C.

9 ml of a 2M NaCl solution are then added and neutralisation is then carried out with 1N NAOH.

The N,O-sulphated heparosan is precipitated with 2 volumes of ethanol, is centrifuged, redissolved in 10 ml of 0.5M NaCl and precipitated again with 2 volumes of ethanol. After centrifuging, the pellet is taken up in a minimum volume of water and dialysed for 15 hours.

Finally, the product is lyophilised.

470 mg of N,O-sulphated heparosan are obtained (Batch 5Cla). The characteristics of this product are identical to those of the N,O-sulphated heparosan (Batch 4) described in Example 4.

Process II: Sulphation with chlorosulphonic acid

The remaining 420 mg of N-sulphated, N-deacetylated heparosan in the form of the tetrabutylammonium salt are dissolved in 8 ml of anhydrous formamide (the mass shown corresponds to N-sulphated, N-deacetylated heparosan in the nonsalified form). The solution is passed through a 15 ml column containing a 4 Å molecular sieve and recovered in a three-necked, round bottom flask fitted with a calcium chloride drying tube. 346 µl of anhydrous pyridine are then added. 256 mg of chlorosulphonic acid in solution in 1 ml of dichloromethane are then run in very slowly while stirring the mixture vigorously and while taking care that the temperature of the reaction mixture does not exceed 35° C. (duration of the addition : 15 minutes). The solution is then stirred for 2 hours at room temperature. 10 ml of 0.5M NaCl are then added and the solution is neutralised with 1N sodium hydroxide solution.

The N,O-sulphated heparosan is precipitated with 2 volumes of ethanol, centrifuged and redissolved in 10 ml of 0.5M NaCl. Subsequently, it is precipitated again with 2 volumes of ethanol and centrifuged. The pellet is taken up in a minimum volume of water and dialysed extensively for 15 hours.

After lyophilising, 430 mg of product, called Batch 5C1b, are obtained.

The characteristics of this low molecular mass N,O-sulphated heparosan are shown in Table XII.

TABLE XII

| | Uronic acid level (µmol/mg) | $NH_2$ level (µmol/mg) | Degree of deacetylation | Degree of sulphation (sulphate/carboxyl ratio) |
|---|---|---|---|---|
| Batch 5C1b | 1.40 | <0.02 | 80% | 2.50 |

The molecular mass distribution of the chains which constitute the N,O-sulphated heparosan of Batch 5C1b was assessed by steric exclusion HPLC according to the method described in Preparation VII and is shown in Table XIII.

$MW_1$, $MW_2$, $MW_3$, $MW_4$ and $MW_5$ have the meanings given for Table IV.

TABLE XIII

| Molecular mass distribution of the product corresponding to Batch 5C1b | | | | |
|---|---|---|---|---|
| $MW_1$ | $MW_2$ | $MW_3$ | $MW_4$ | $MW_5$ |
| 11,881 | 9116 | 7253 | 5513 | 3056 |

This product consists of 70% of chains having a molecular mass of between 8792 and 5900 D.

We claim:

1. N,O-sulphated heparosans of chains or a mixture of chains of molecular mass between $1.5 \times 10^4$ and $4.0 \times 10^6$ Da, the molecular mass being determined by exclusion HPLC, which comprise repeated disaccharide units of formula I:

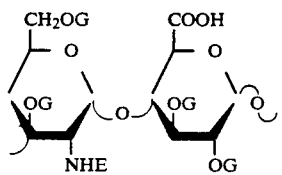

in which:
E represents an acetyl group in 0 to 80% of the disaccharide units, and a sulphate group or a hydrogen atom in the remaining disaccharide units,
G represents a hydrogen atom or a sulphate group, or pharmaceutically acceptable salts thereof.

2. N,O-Sulphated heparosans according to claim 1, wherein the degree of sulphation, expressed as the sulphate/carboxyl ratio, is between 1.5 and 3.0.

3. N,O-Sulphated heparosans according to claim 1, characterised in that the acetyl group of the disaccharide units is present at a level less than or equal to 60%.

4. N,O-Sulphated heparosans according to claim 1, which contain less than 0.2 μmol/mg of free amino group ($NH_2$).

5. N,O-Sulphated heparosans according to claim 1, consisting of at least 70% by mass of chains having a molecular mass of between $1.0 \times 10^5$ and $5.0 \times 10^5$ D.

6. N,O-Sulphated heparosans according to claim 1, consisting of at least 70% by mass of chains having a molecular mass of between $2.5 \times 10^4$ D and $2.5 \times 10^5$ D.

7. N,O-Sulphated heparosans according to claim 1, consisting of at least 70% by mass of chains having a molecular mass of between $2.0 \times 10^4$ D and $1.0 \times 10^5$ D.

8. A N,O-Sulphated heparosan composition, characterised in that it contains at least 70% by mass of a N,O-sulphated heparosan according to claim 1.

9. The pharmaceutical composition containing, as active ingredient, a N,O-sulphated heparosan according to claim 1, in combination or as a mixture with an inert, pharmaceutically acceptable excipient.

10. The pharmaceutical composition containing, as active ingredient, a N,O-sulphated heparosan according to claim 8, in combination or as a mixture with an inert, pharmaceutically acceptable excipient.

11. The pharmaceutical composition according to claim 9, which can be used for controlling clotting.

12. N,O-sulphated heparosans of claim 1 wherein E represents an acetyl group in 0 to 80% of the dissacharide units and a sulphate group in the remaining dissacharide units.

13. N,O-sulphated heparosans according to claim 1 wherein the degree of sulphation, expressed as sulphate/carboxyl ratio, is from 1.5 to 3.0, and the two ends, reducing and non-reducing, of the chains of the N,O-sulphated heparosans are sulphated or non-sulphated uronic units, sulphated or non-sulphated glucosamine units, or sulphated or non-sulphated N-acetylglucosamine units.

* * * * *